(12) United States Patent
Chang (10) Patent No.: US 8,278,629 B2
(45) Date of Patent: Oct. 2, 2012

(54) OBSERVATION CHAMBER FOR STUDYING TEMPERATURE-DEPENDENT EVENTS AND METHOD THEREOF

(75) Inventor: Yen-Chung Chang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 428 days.

(21) Appl. No.: 12/543,812

(22) Filed: Aug. 19, 2009

(65) Prior Publication Data

US 2011/0042583 A1 Feb. 24, 2011

(51) Int. Cl.
*G01N 21/64* (2006.01)
*G01T 1/10* (2006.01)
(52) U.S. Cl. ............... 250/458.1; 250/459.1; 250/461.2
(58) Field of Classification Search ............... 250/459.1, 250/461.2, 458.1
See application file for complete search history.

(56) References Cited

U.S. PATENT DOCUMENTS

2009/0173889 A1* 7/2009 Costantino et al. ......... 250/459.1
2010/0044586 A1* 2/2010 Duhr et al. ............... 250/459.1

OTHER PUBLICATIONS

Conly L. Rieder et al., Cold-Shock and the Mammalian Cell Cycle, Cell Cycle 1:3, 169-175, May/Jun. 2002.
Larry A. Sonna et al., Molecular Biology of Thermoregulation Invited Review: Effects of heat and cold stress on mammalian gene expression, J Appl Physiol 92: 1725-1742,2002.
Fredrik Asztely et al., Extrasynaptic Glutamate Spillover in the Hippocampus: Dependence on Temperature and the Role of Active Glutamate Uptake, Neuron, vol. 18, 281-293, Feb. 1997.
Bernardo L. Sabatini et al., Timing of Neurotransmission at fast synapses in the mammalian brain, Nature, Nov. 14, 1996, vol. 384, pp. 170-172.
Ben N. G. Giepmans et al., The Fluorescent Toolbox for Assessing Protein Location and Function, Science, vol. 312, Apr. 14, 2006, pp. 217-223.
Laurent Guillaud et al., STOP Proteins are Responsible for the High Degree of Microtubule Stabilization Observed in Neuronal Cells, The Journal of Cell Biology, vol. 142, No. 1, Jul. 13, 1998 167-179.
Yanping Yan et al., In vivo assay of presynaptic microtubule cytoskeleton dynamics in *Drosophila*, Journal of Neuroscience Methods 162 (2007) 198-205.
James G. McNally et al., Quantitative FRAP in Analysis of Molecular Binding Dynamics in Vivo, Methods in Cell Biology, vol. 85, pp. 329-351.
Veronica Al. Alvarez et al., Anatomical and Physiological Plasticity of Dendritic Spines, Annu. Rev. Neurosci. 2007, vol. 30, pp. 79-97.
Jennifer N. Bourne et al., Balancing Structure and Function at Hippocampal Dendritic Spines, Annu. Rev. Neurosci. 2008, vol. 31, pp. 47-67.
Hui-Hsuan Cheng et al., Cold-Induced Exodus of Postsynaptic Proteins From Dendritic Spines, Journal of Neuroscience Research, 2009, vol. 87, pp. 460-469.

* cited by examiner

*Primary Examiner* — David Porta
*Assistant Examiner* — Faye Boosalis
(74) *Attorney, Agent, or Firm* — WPAT, P.C.; Anthony King (57) ABSTRACT

Live-cell imaging chambers are used in a wide range of cell biology research. Recently, chambers capable of taking high-resolution and time-lapse images of live cells have been developed and become commercially available. However, since most of these chambers are designed to maintain a thermally stable environment for the cells under study, it is usually very difficult to use them to study temperature-dependent cellular events. The present invention provides a live-cell observation equipment for a non light-transmitting microscope to study temperature-dependent events and method thereof.

16 Claims, 9 Drawing Sheets

OBSERVATION CHAMBER FOR STUDYING TEMPERATURE-DEPENDENT EVENTS AND METHOD THEREOF

FIELD OF THE INVENTION

The present invention provides a live-cell observation equipment for a non light-transmitting microscope to study temperature-dependent events and method thereof.

BACKGROUND OF THE INVENTION

Live-cell imaging chambers have played a critical role in recent cell biology research. A variety of designs for such chambers have been made since mammalian cell culture techniques were developed in the early twentieth century. These designs vary in complexity from simply covering specimen on a microscope slide with a coverslip to sophisticated perfusion chambers that enable living specimens to remain viable for a significant length of time outside the incubator. At present, a variety of chambers for taking high resolution and time-lapse images of live cells using phase contrast, differential interference contrast (DIC) and fluorescence microscopy are commercially available.

The basic design of most live-cell imaging chambers consists of a sandwich structure made from two transparent plates separated by a rubber O-ring or similar spacer and a holder that can be made from a variety of different materials and houses the sandwich structure. Various modified versions of this basic design have also been manufactured in recent years. To keep cells viable in a live-cell imaging chamber for a prolonged period of time, the cells in the chamber need to be kept in an environment that has a regulated temperature, to be maintained a constant pH, to be provided with sufficient $O_2$ and also to be supplied with an adequate energy supplies. The designs used to control the temperature of a live-cell chamber adequately include a Peltier heat pump, resistive coils, circulating warm water, circulating warm air, a climate controlled box, a stage warmer and an objective-lens heater with indium-tin oxide coated glass (Rieder C. L. and Cole R. W. 2002. Cold-Shock and the Mammalian Cell Cycle. Cell Cycle 1: 169-175.). Fresh medium at the preferred pH range and containing sufficient $O_2$ and energy supplies typically flows through the chamber and is driven by gravity, a peristaltic pump or a syringe pump (Rieder C. L. and Cole R. W. 2002. Cold-Shock and the Mammalian Cell Cycle. Cell Cycle 1: 169-175.).

A change in temperature has profound influences on the physiology of cells. Cold and heat stress may affect gene expression, immune function and the cell cycle (Sonna L. A. et al., 2002 Molecular Biology of Thermoregulation Invited Review: Effects of heat and cold stress on mammalian gene expression. J appl Physiol 92: 1725-1742.). At a molecular level, the diffusion rate of ions, the functioning of ion channels, the level of enzyme activity, the association-disassociation interactions between proteins and the polymerization-depolymerization reactions of cytoskeleton may be influenced by temperature change (Asztely F. et al., 1997. Extrasynaptic Glutamate Spillover in the Hippocampus: Dependence on Temperature and the Role of Active Glutamate Uptake. Neuron 18: 281-293; Sabatini Bernardo L. and Regehr W. G. 1996. Timing of neurotransmission at fast synapses in the mammalian brain. NATURE 384: 170-172.). Most modern live-cell chambers have been designed with the focus on thermal stability rather than rapid temperature change, and these chambers are therefore not suitable for studying the effects of temperature change on cells.

BRIEF DESCRIPTION OF DRAWINGS

FIG. 1 illustrates an exploded view of the live-cell observation chamber.
- a: stainless steel screws, 5 mm in diameter and 3 mm in length at the head region, 3 mm in diameter and 12 mm in length at the stem region
- b: aluminum fixation plate, 44×7×0.5 mm
- c: circular glass coverslip, 24 mm in diameter, 0.17 mm in thickness
- d: silicon O-ring, inner diameter 18 mm, outer diameter 24 mm, cross diameter 2.5 mm
- e: microchamber plate, 76×32×4 mm containing a circular groove (e-1, 3 mm wide, 2.5 mm deep), a circular opening (e-2, 10 mm in diameter, 3.6 mm deep) and a circular opening (e-3, 4 mm in diameter, 2 mm deep) and three holes (1 mm in diameter) labeled as 1, 2, 3
- f: thermoelectric Peltier effect heat pump, 20×20×5 mm
- g: supporting aluminum blocks, 25×10×5 mm
- h: circular plate, 76×54×6 mm containing an open channel (4 mm wide, 4 mm deep) and four holes (3 mm in diameter)
- i: inlet and outlet of ice-cold water (1 mm in diameter)
- j: glass plate, 76×54×1 mm

FIG. 4 illustrates reversible temperature changes of the medium in the live-cell observation chamber. (A) When the chamber is observed using a confocal microscope under a dry lens, the temperature of the medium in the chamber could be changed rapidly and reversibly between 37° C. and 4° C. with heating and cooling rates of 0.35±0.04° C./s and 0.14±0.02° C./s (mean±S.D. of n=5), respectively. (B) Under an oil-immersion lens, the temperature of the medium in the chamber could be changed reversibly between 37° C. and 8° C. with heating and cooling rates of 0.25±0.02° C./s and 0.09±0.01° C./s (mean±S.D. of n=5), respectively. The ice-cold water in the circulation plate was turned on and off during the cooling and heating phases, respectively.

FIG. 5 illustrates the exchanging of the medium in the live-cell observation chamber. The fluorescent dye, FITC (706 µl), was added to the chamber (volume of 326 µl) via the sample injection valve and changes in the integrated fluorescence intensity in the circular areas A and B (0.79 mm in diameter), as indicated in the inset, were monitored (intensities in the A and B areas as the thin and thick curves, respectively). The fluorescent dye started to flow into the chamber at 5 s after the injection valve was closed. The fluorescence intensity in the chamber area reached a plateau at 5 s later and remained at the plateau level for another 9 s. After that, the fluorescence intensity returned to that at the beginning of the study prior to sample injection in about 150 s.

FIG. 6 illustrates continuous monitoring of neurons using the live-cell observation chamber. Fluorescence images of a neuron transfected with YFP-α-tubulin were taken every 2 min for a period of 30 min. Another image of the same neuron was taken after adjusting the focus manually. In this experiment, it only required the adjustment the objective lens in the Z axis for 0.175 μm, but not the X or Y axis. (A) Image is taken at 0 min. (B) Image is taken at 32 min after refocusing. Scale bar: 10 μm.

FIG. 7 illustrates FRAP of YFP-α-tubulin in a hippocampal neuron cell body. (A) Representative time course images of YFP-α-tubulin. Black circles indicate the regions that were photobleached and subsequently monitored for fluorescence recovery. The panel shows pre-bleach (0 s), immediately after bleach (12.6 s) and post-bleach (420.6 s) images. Scale bar: 10 μm. (B) Normalized FRAP curve of YFP-α-tubulin. Pre-bleach intensity was set to 100%. Immediately after bleaching at 37° C. and 13° C., the YFP-α-tubulin fluorescence intensity in the photobleached region dropped to 33.5±1.9% and 44.7±0.8%, respectively. During the first 15 after photobleaching, fluorescence recovered to 53.2±3.2% and 66.3±1.8%, respectively. Finally over the nearly 8.5 min and 2.5 min observation periods, the fluorescence slowly recovered to 68.3±3.8% and 79.3±3.1% of the initial intensity, respectively. N=3.

FIG. 8 illustrates temperature-dependent localization of α-tubulin in dendritic spines. Cultured rat hippocampal neurons at DIV 17 expressing YFP-α-tubulin (green) and DsRed1-N1 (red) were maintained in a live-cell observation chamber with the temperature of medium kept at 37° C. except for a period of 6 min at 13° C. (A) Images of a portion of a DsRed1-N-1-(right column panels) and YFP-α-tubulin-(middle column panels) expressing neuron taken at 37° C. (top row panels), six minutes after the temperature of the medium was cooled to 13° C. (middle row figures) and 6 min after the medium was warmed to 37° C. (bottom row figures) again. The panels in the left column are the color merges of those in the middle and right columns for each condition. Scale bar: 2 μm. (B) Summary and schematic representation of the various changes in YFP-α-tubulin (blue) in dendritic spines before, during and after an intermittent period of cold. Changes of YFP-α-tubulin in spines are categorized into three types (from top to bottom): reversibly receding from the spine structure (indicated by arrow in A), the generation of new YFP-α-tubulin-positive spines and unchanged spines (indicated by arrowhead in A). Data are the means±S.D. from 144 spines in 7 neurons.

FIG. 9 illustrates caffeine-induced exit of α-tubulin from dendritic spines. Cultured rat hippocampal neurons at DIV 17 co-expressing YFP-α-tubulin (green) and DsRed1-N1 (red) were maintained in a live-cell observation chamber with the temperature of medium kept at 37° C. Medium containing 10 mM caffeine was then introduced into the chamber. 10 min later, the caffeine-containing medium was replaced by fresh medium. (A) Images of a portion of a DsRed1-N1-(right column panels) and YFP-α-tubulin-(middle column panels) expressing neuron taken before (top row panels), during (middle row figures) and after (bottom row figures) caffeine application. The panels in the left column are the color merges of those in the middle and right columns for each condition. Scale bar: 2 μm. (B) Summary and schematic representation of the various changes in YFP-α-tubulin (blue) in dendritic spines before, during and after 10 mM caffeine treatment. Changes of YFP-α-tubulin in spines are categorized into three types (from top to bottom): reversibly receding from the spine structure (indicated by arrows in A), the generation of new YFP-α-tubulin-positive spines and unchanged spines (indicated by arrowhead in A). Data are means±S.D. from 122 spines in 6 neurons.

SUMMARY OF THE INVENTION

The present invention provides a cell observation equipment for a non light-transmitting microscope.

The present invention also provides a method for observing the influence to a cell by changing the temperature rapidly.

DETAILED DESCRIPTION OF THE INVENTION

The live-cell observation chamber described here (FIG. 1) consists of an open circular chamber that can be covered from the top by a glass-coverslip containing cultured neurons with its neuron-containing side facing the interior of the chamber. The chamber is then filled with the culture medium in a static or circulating manner, and the bottom side of the chamber is in tight contact with a non-transparent heating/cooling pump. This design allows the taking of fluorescence images of the live neurons attached to the glass-coverslip using most commercially available up-right epi-fluorescence and confocal microscopes. This is because the excitation and emission lights in these microscopes take the same route in and out of the cover-glass-covered side of the chamber. However, this chamber lacks the capability of taking bright-field images of the neurons that requires the use of a chamber transparent on both the top and bottom sides to allow the passage of the incident and reflected light. In most experiments wherein a fluorescence microscope is used, a bright-field image of the neurons in study is usually taken to accompany their fluorescence images; this is so that the former one is able to serve as the referencing background for the distribution of the fluorescent marker(s) of interest in the same neurons. This lack of a capability of taking bright-field images using the live-cell observation chamber described here can be overcome by exploiting recent advances in fluorescence tagging technology (Giepmans Ben N. G et al., 2006 The Fluorescent Toolbox for Assessing Protein Location and Function. SCIENCE 312: 217-224.). This technology makes it feasible and convenient to express two or more fluorescence molecules, such as proteins tagged with fluorescence and fluorescence markers associated with various intracellular organelles, in the same cells. The fluorescence image of a neuron expressing a cytosolic fluorescence protein (such as DsRed1-N1 in FIG. 3) is able to reveal the neuron's morphology, as good as or even better than its bright-field counterpart. Therefore, when a neuron is simultaneously expressing fluorescence-tagged molecules of interest together with a fluorescent cytosolic protein, the distribution of the former molecules and the morphology of this neuron may be examined simply by using the different channels that respectively excite and detect the emissions from the various fluorescence tags (e.g., FIGS. 7 and 8). By doing so, the live-cell observation chamber describe here, which is transparent on only one side, is available for use in most cell biology studies and is equivalent to other chambers that are transparent on both the top and bottom sides.

Figure 4:
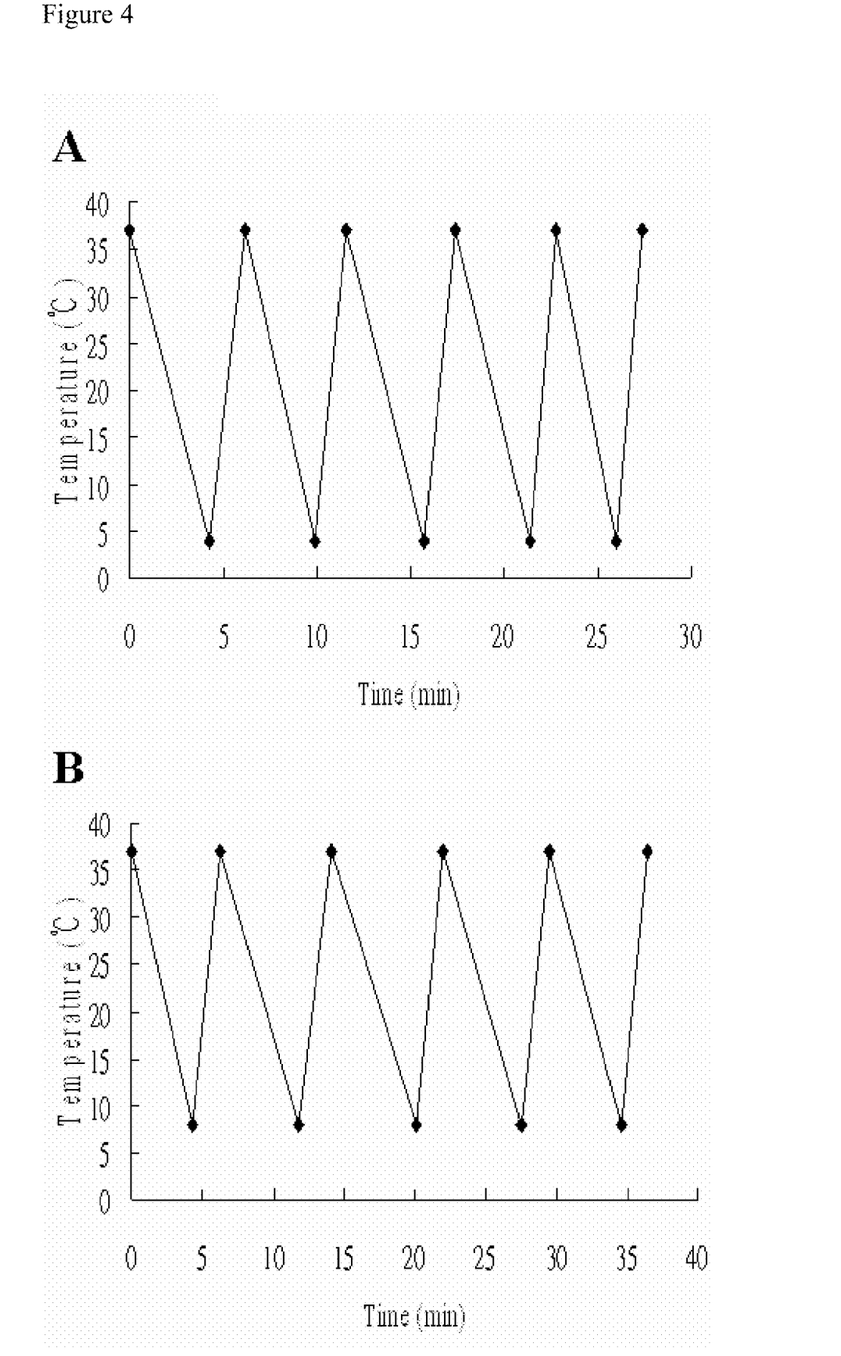

By sacrificing the capability of taking bright-field images, the live-cell observation chamber reported here is able to perform a rather unique function. Since a heating/cooling pump is placed underneath the chamber, the temperature of the medium in the chamber can be heated and cooled rapidly and reversibly between 37° C. and 4° C. (or even wider ranges on both ends if needed) when a dry lens is used and between 37° C. and 8° C. (or even an wider range at the higher temperature end but not at the lower temperature end) when an oil-immersion lens is used (FIG. 4). The difference between the temperature ranges of the medium in the chamber when a dry or oil-immersion lens is used is mainly due to the heat dissipation between the chamber and an oil-immersion lens, which does not occur between the chamber and a dry lens. Nevertheless, with the help of circulating ice-cold water through a channel in an aluminum plate underneath the heating/cooling pump, the temperature of the medium in the chamber can still be lowered to 8° C. when an oil-immersion lens is used.

Figure 8:
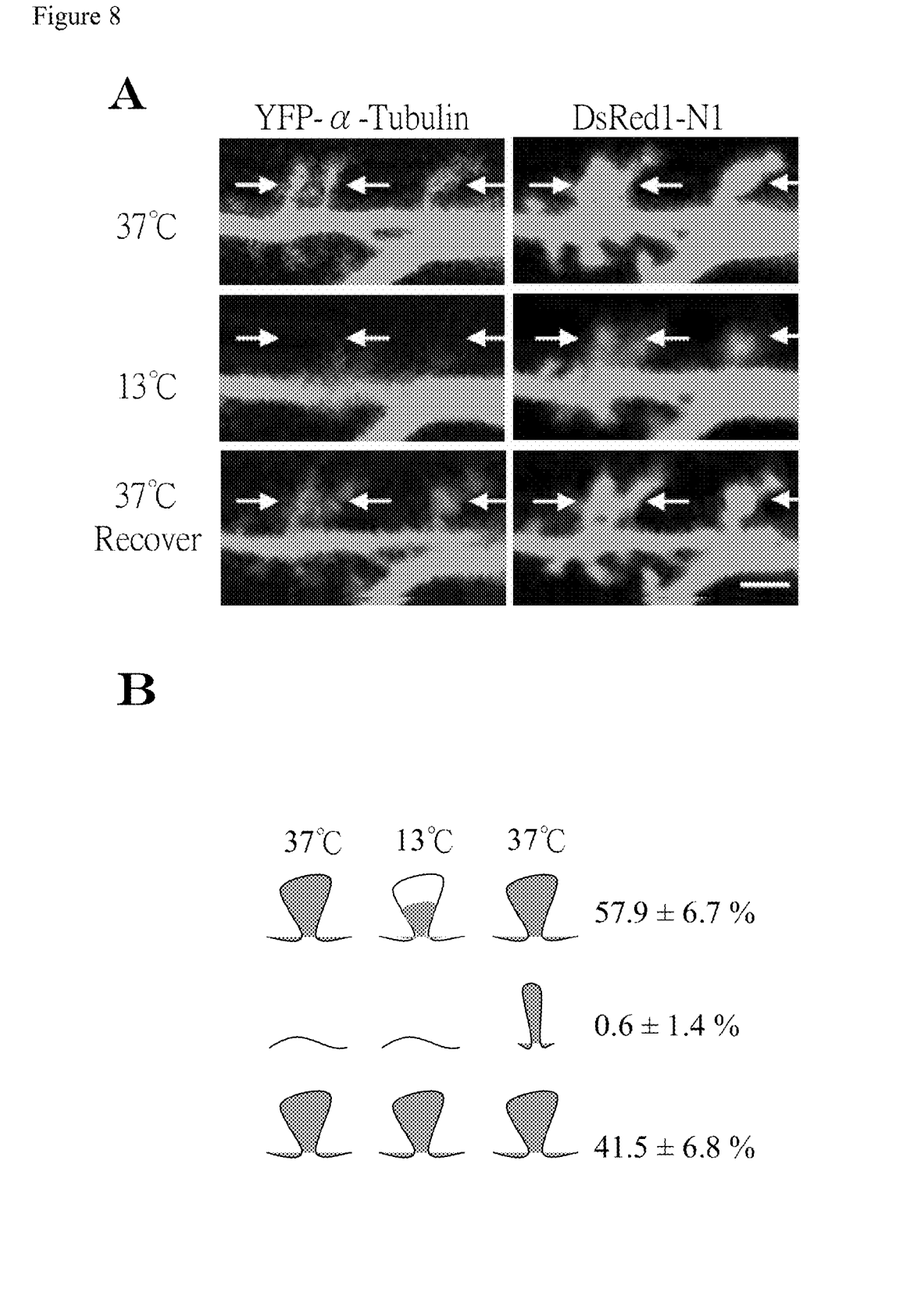
Figure 9:
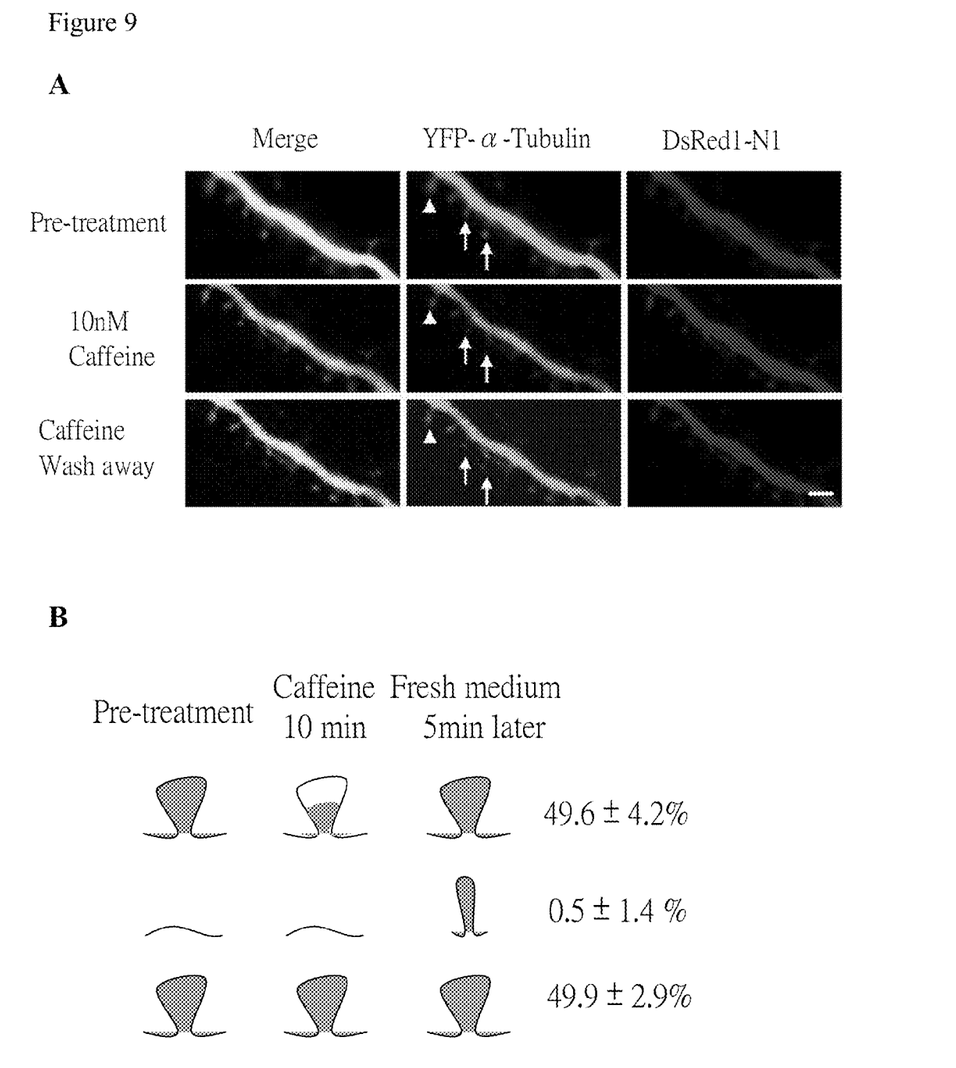

This unique capability of our live-cell observation chamber of heating and cooling the medium in the chamber rapidly and reversible has been exploited here to study cold-induced effects on the dynamics of the microtubule cytoskeleton and on the localization of α-tubulin in the dendritic spines of neurons. The stability of the microtubule cytoskeleton in neurons has been found to be regulated by a variety of microtubule-associated proteins, such as MAPs and STOP (Guillaud L. et al., 1998 STOP Proteins are Responsible for the High Degree of Microtubuline Stabilization Observed in Neuronal Cells. The Journal of Cell Biology 142: 167-179.). A FRAP study of the α-tubulin-GFP-containing microtubules in the presynaptic terminals of Drosophila neuromuscular junctions has indicated that the fast and slow phase (the first and second exponential terms in the equation shown in Table 1) of the fluorescence recovery after photobleaching are respectively related to the movement by diffusion of tubulin dimers and the dynamic turnover of tubulin dimers in microtubules (Yan Y. P. and Broadie K. 2007. In vivo assay of presynaptic microtubule cytoskeleton dynamics in Drosophila. Journal of Neuroscience Methods 162: 198-205.). Here, the present invention found that by lowering the temperature from 37° C. to 13° C., both $\tau_{1/2}$ values of the fast and slow phases of fluorescence recovery after photobleaching of the YFP-α-tubulin in cultured rat hippocampal neurons became smaller. Furthermore, the mobile fraction of the YFP-α-tubulin in neurons maintained at 13° C. was greater than that of neurons maintained at 37° C. These results are consistent with an increase in the dynamics of microtubules in neurons upon cooling. Using the same chamber, it was found that α-tubulin exited from more than half of the dendritic spines in cultured rat hippocampal neurons when the medium temperature was lowered from 37° C. to 13° C. (FIG. 8). By coupling the perfusion system with a sample injection valve (FIG. 2), this chamber was also able to be used in pharmacological studies, in this case a study of the caffeine-induced exit of YFP-α-tubulin from a large proportion of the dendritic spines (FIG. 9). The mechanism(s) underlying these cold- and caffeine-induced changes to neurons is unclear at present and needs to be investigated further in the future. These results nevertheless clearly indicate the usefulness of our live-cell observation chamber described here for the study of temperature- and drug-induced effects on live neurons.

Figure 5:
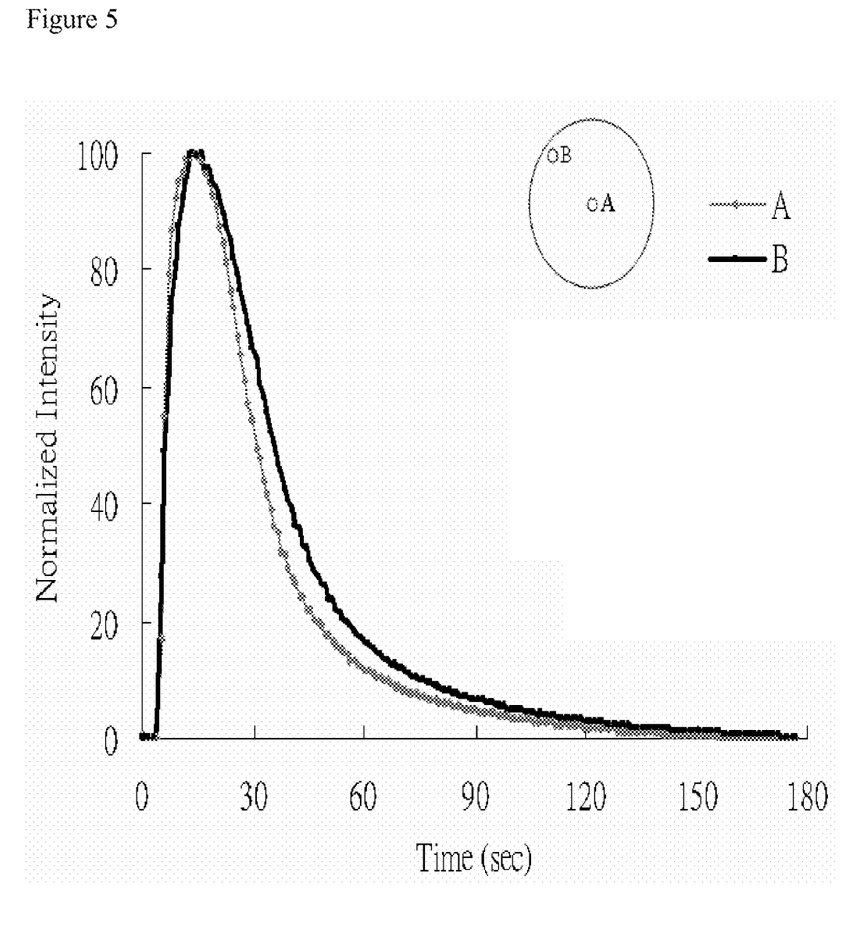

In conclusion, the present invention provides here a live-cell observation chamber that is easy to assemble and dissemble without the need for any special tools (FIG. 1), that can fit almost all of the commercially available up-right epi-fluorescence or confocal microscopes, that can be sterilized by simply soaking in alcohol, that is leak-free and that allows rapid and reversible changes in the temperature and composition of the medium to be induced in the medium surrounding the neurons used in this study (FIGS. 4 and 5). Conceivably, this observation chamber will become a useful tool for neuroscientists who conduct in vivo cell biology experiments.

The present invention provides a cell observation equipment for a non light-transmitting microscope, comprising: (a) a coverslip; (b) a sealed material; (c) a microchamber plate containing a circular groove embedded with the sealed material; an inner circular opening to load and circulate the medium; and a plurality of pipes connecting with the inner circular opening; and (d) a thermal effect heat pump placed below the microchamber plate by way of contacting directly.

In preferred embodiment of the present invention, the non light-transmitting microscope is a confocal microscope or a fluorescence microscope.

The thermal effect heat pump is a thermoelectric Peltier effect heat pump acting as a heater or a cooler by switching the polarity of input DC current.

The microchamber plate is made of a transparent and a non heat conducting material and the transparent and non heat conducting material is polymethyl methacrylate.

The sealed material is silica gel or rubber-like cushion.

The pipes include the pipe for inflow of the medium; the pipe for injection of the sample; the pipe for outflow of the medium and the pipe for temperature detection. The inflow and outflow of the medium is driven by the mechanical power.

The cell observation equipment can further comprise a circulating plate attached below the thermal effect heat pump directly. The circulating plate contains a channel for flow of the cooling liquid. The flow of the cooling liquid is used to enhance the cooling effect of the thermal effect heat pump.

The cell observation equipment is applied to change the temperature of the medium rapidly and reversibly.

The present invention also provides a method for observing the influence to a cell by changing the temperature rapidly, the steps comprising: (a) culturing the cell attached on one side of the coverslip; (b) constructing the cell observation equipment of the microchamber plate, the sealed material, the coverslip with the cell faced to a microchamber plate, and the thermoelectric Peltier effect heat pump; (c) inputing a current to the pump and adjusting a direction of the current to heat or cool the microchamber plate; and (d) observing a cell performance after heating or cooling rapidly.

The method can further comprise the step of attaching the circulating plate below the thermoelectric Peltier effect heat pump to enhance the cooling effect of the thermoelectric Peltier effect heat pump.

EXAMPLES

The examples below are non-limiting and are merely representative of various aspects and features of the present invention.

Materials and Methods

Design and operation of the live-cell observation chamber

Figure 1:
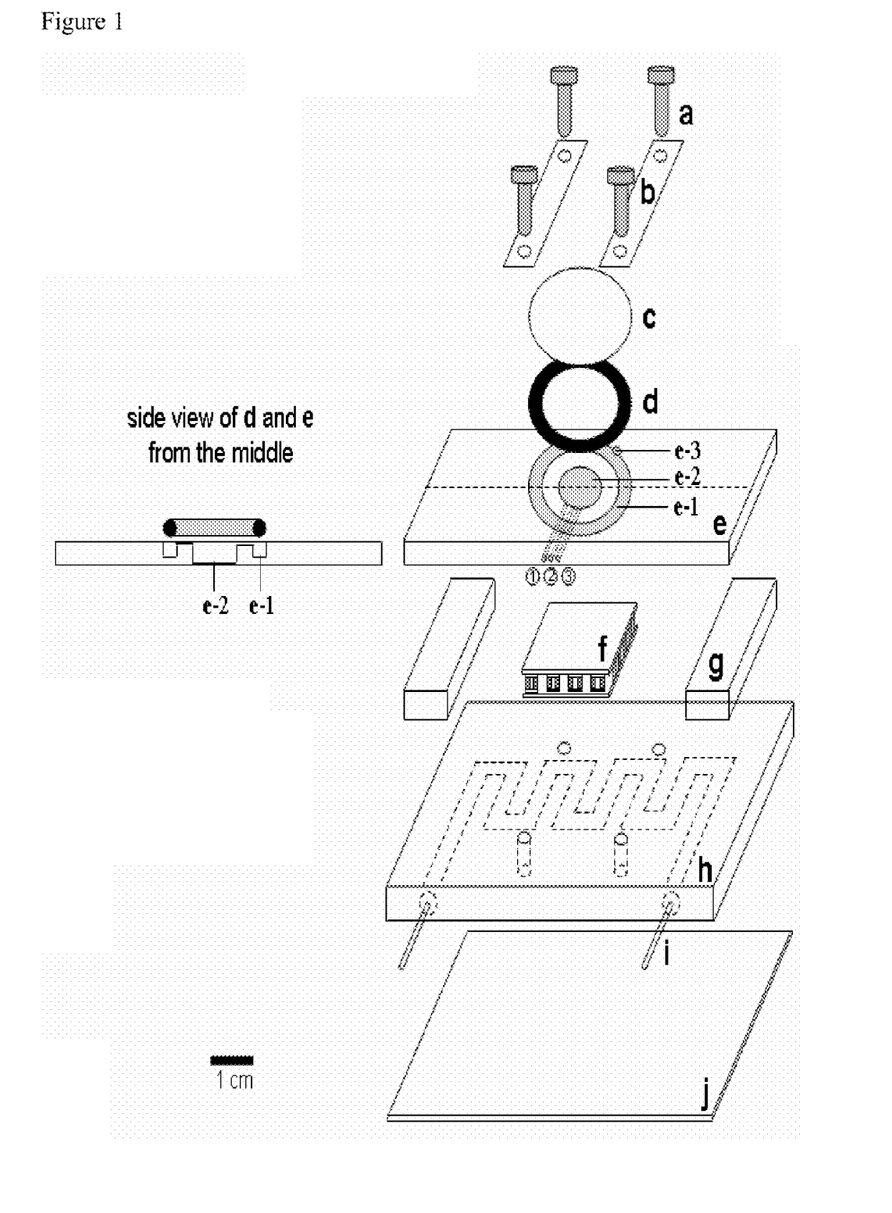
Figure 2:
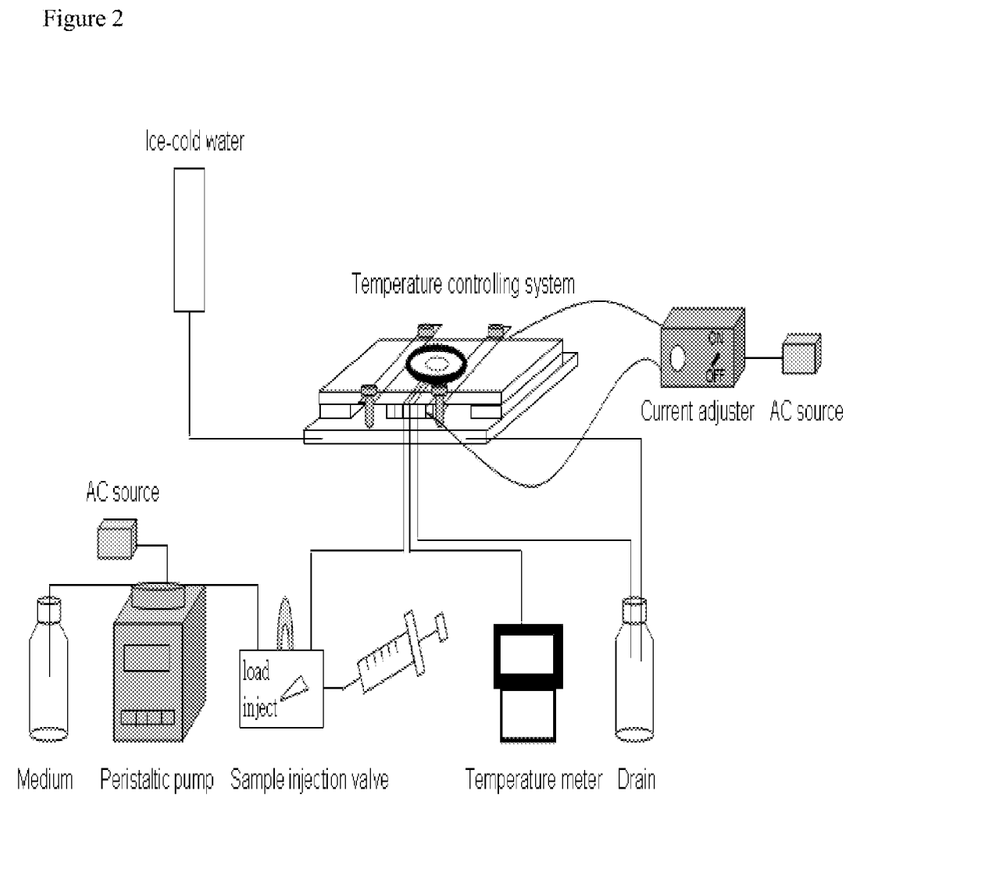
FIG. 2 illustrates a cartoon showing how the accessory parts are connected to the live-cell observation chamber during operation. These accessory parts include a peristaltic pump (Minipuls 3, Gilson Inc., USA), a reservoir and a drain of ice-cold water, a sample injection valve, a temperature meter and a current adjuster.

The design of the live-cell observation chamber and a list of its components were shown in FIG. 1. FIG. 2 was a cartoon illustrating how this chamber is connected to the various accessory parts during the experimental sessions. The aluminum fixation plates (b), microchamber plate (e), supporting blocks (g) and circulating plate (h) were made by the Scientific Instrument Center of National Tsing Hua University (Hsinchu, Taiwan). Neurons were grown on the surface of a glass coverslip (c), which was fastened to the top of the microchamber plate (e) by tightening the stainless steel screws through the aluminum fixation plates (b) to the top of circulating plate (h). A silicon O-ring (d) was placed between the glass coverslip and microchamber plate to keep the chamber leak-free. The microchamber plate (e) was made from polymethyl methacrylate and contained a circular groove (e-1) and a concentric inner circular opening (e-2). The circular groove (e-1, 3 mm wide and 2.5 mm deep) was 21 mm in its inner diameter and made to house the silicon O-ring (d). The inner circular opening (e-2) was 10 mm in diameter and 3.6 mm deep. A third circular opening (e-3), 4 mm in diameter and 2 mm deep, was made next to the groove (e-1) to help mount and remove the glass coverslip (c) to and from the chamber. Three holes (1 mm in diameter and respectively labeled as 1, 2 and 3) were drilled through the side to the inner circular opening (e-2) allowed the placing of the thermocouple probe (SA1XL-K, Omega Engineering Inc., USA) in the middle hole (hole 2) and for the circulation of medium into and out of the central circular chamber (via holes 1 and 3) by a peristaltic pump (FIG. 2). The thermocouple probe was in turn connected to a temperature meter (Model HHM1, Omega Engineering Inc., USA) (FIG. 2). A thermoelectric Peltier effect heat pump (f) (TECI-3103, Centenary Materials, Taiwan) was placed in between the microchamber plate and aluminum circulating plate (h). The function of this pump was to act as a heater or cooler, which was selected by switching the polarity of input DC current. The heating/cooling output was controlled by manually adjusting the DC current from a current adjuster (FIG. 2). Two aluminum supporting blocks (g) were also placed between the microchamber plate (e) and the circulating plate (h). The circulating plate was made from aluminum and contained an open channel (4 mm wide and 4 mm deep), with its open side facing the bottom. Four holes (3 mm in diameter) were drilled on the plate to hold the stainless steel screws (a). A piece of glass plate (i) was glued to the bottom side of the circulating plate (h). Ice-cold water could flow through the channel of the circulating plate (h) pulled by gravity when the chamber operated in the cooling mode (FIG. 2). When in the heating mode, the flow of ice-cold water was stopped. Drugs could be added to the microchamber via a sample injection valve (Bio-Chem Fluidics, USA) (FIG. 2).

Pregnant Sprague-Dawley rats were obtained from Bio-LASCO Taiwan Co., Ltd (Taipei, Taiwan). $Ca^{2+}$-free, $Mg^{2+}$-free Hank's balance salt saline (HBSS), Minimum Essential Medium (MEM) powder, Neurobasal medium, B-27 supplement, horse serum and penicillin/streptomycin were purchased from GIBCO (Invitrogen, CA, USA). Papain, DNaseI, poly-L-lysine, L-glutamine, L-glutamic acid, cytosine-beta-D-arabinofuranoside (Ara-C), HEPES and glucose were bought from Sigma (Sigma-Aldrich, Mo., USA). Fetal bovine serum (FBS) was obtained from Biological Industries (Haemek, Israel).

Rat Hippocampal Neuronal Culture

Primary hippocampal cultures were prepared from Sprague-Dawley rat fetuses at embryonic day 18. In brief, hippocampi were dissected from rat embryos and treated with papain (10 units/ml) at 37° C. for 15 min. Afterward horse serum was added to the cell mixture to stop the papain reaction. After centrifugation at 1500 rpm for 5 min, the supernatant was aspirated, and the pellet was resuspended in MEM and then filtered through a cell strainer (pore size of 70 μm). The percentage of viable cells was quantified by cell density counting using a hemocytometer after trypan blue staining. Cells at the density of $1 \times 10^5$ cells/$cm^2$ were plated on glass coverslips (24 mm in diameter) pre-coated with poly-L-lysine, which were then placed in 6-well culture plates and kept at 37° C. and under 5% $CO_2$/95% $O_2$ in a humidified incubator. One day later, the culture medium was replaced with NB/B27 (with additional 0.025 mM glutamate, Gibco) and subsequently replaced with NB/B27 every 4 days. On DIV 3, the cells were treated with 5 μM Ara-C for 1 day to curtail the growth of glial cells.

DsRed1-N1 and YFP-α-Tubulin Transfection

The YFP-α-tubulin plasmid was kindly provided by Dr. Jan Ellenberg of the European Molecular Biology Laboratory at Heidelberg, Germany. The DsRed1-N1 plasmid was kindly provided by Dr. Tzong-Yuan Wu (Department of Bioscience Technology, Chung Yuan University, Taiwan). The plasmids were transfected into hippocampal neurons on DIV4-6 using a kit, ProFection Mammalian Transfection Systems-Calcium Phosphate (Promega Corporation, PA, USA). Briefly, the cells were placed in conditioned culture media 1 hr prior to transfection. The plasmid/calcium phosphate precipitate was prepared by mixing one volume of plasmid in 2M calcium chloride with an equal volume of 2×HBS (280 mM NaCl, 1.5 mM $Na_2HPO_4$, 50 mM Hepes at pH7.10). After being kept at room temperature for 30 min, the precipitate were added as droplets to each well and mixed gently. After being kept in the incubator for 1 hr, cells were washed with fresh culture medium, placed in fresh culture medium and then returned to incubator for later investigation.

Fluorescence Recovery after Photobleaching (FRAP)

The FRAP experiments were performed by confocal laser scanning microscopy (LSM 510, Carl Zeiss, Inc., NY, USA) with a 63×/1.4NA oil-immersion objective lens. Cells were kept at 37° C. or 13° C. using the live-cell observation chamber described in this paper. Bleaching was performed on a circular region, 3.9 μm in diameter, by a 488 nm line from a 40 mW argon laser operating at 100% laser power. Fluorescence recovery was monitored at low laser intensity (4% of the 40 mW laser). Frames (512×512 pixels) were captured using the 12-bit detector mode. The scan speed was set at 9 (1.6 μs/pixel) for fast acquisition in order to minimize photobleaching during image acquisition. A FRAP imaging protocol was developed consisting of three pre-bleach images and fifty post-bleach images at 37° C. FRAP performed at 13° C. was similar but only forty-one post-bleach images were recorded. At the initial phase of post-bleach fluorescent recovery, images were taken every 3 s until 120 s. Thereafter, images were recorded every 30 s in order to minimize unintentional bleaching during imaging. Three separate FRAP datasets were obtained from three neurons; these were then averaged to generate a single FRAP curve. The FRAP data processing was performed following a method described in an earlier report (McNally J. G 2008. Quantitative FRAP in Analysis of Molecular Binding Dynamics In Vivo. METHODS IN CELL BIOLOGY 85: 329-351.) and carried out by the Kinetic Analysis software of the LSM 510.

Confocal Imaging and Data Analysis

Images were obtained by confocal laser scanning microscopy (LSM 510, Carl Zeiss, Inc., NY, USA) using a 63×/1.4NA oil-immersion objective lens or a 20× dry lens. In this study, protrusions longer than 6 μm on the processes of cultured rat hippocampal neurons were regarded to be branches or fillopodia and those shorter than 6 μm were considered to be dendritic spines. The data was analyzed by Student's t-test.

Results

Figure 3:
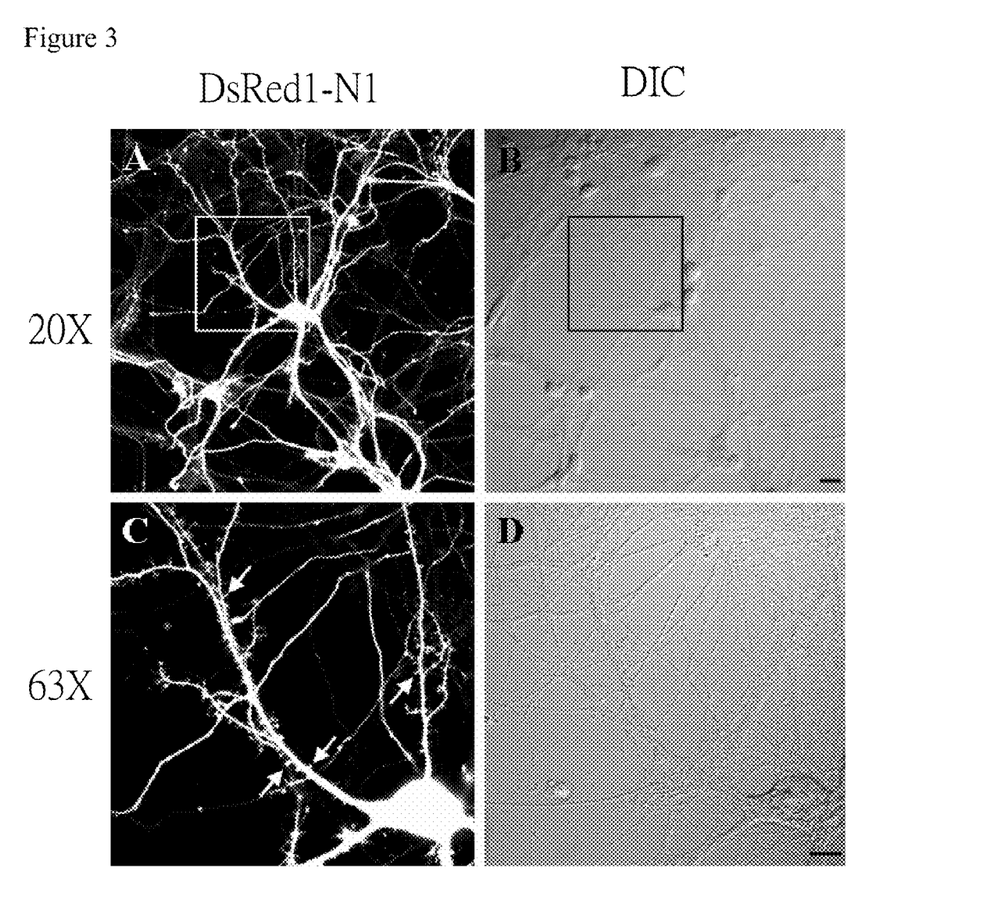
FIG. 3 illustrates the fluorescent (A, C) and bright-field (B, D) images of neurons expressing DsRed1-N1. Cultured rat hippocampal neurons at DIV 17 expressing DsRed1-N1 were fixed at 37° C. and examined with a 20× dry lens (A, B) and a 63× oil-immersion lens (C, D) under a confocal microscope. Left and right figures are the fluorescent and DIC images of the same field. (C) and (D) are the images of the areas enclosed by the squares in (A) and (B) at higher magnification. Dendritic spines were clearly discernable in (C) and are indicated by arrows. Scale bars in A and B and in C and D: 20 µm and 10 µm, respectively.

The fluorescent cytosolic protein DsRed1-N1 revealed the detailed morphology of the neurons Although the chamber described here does not allow the capturing of bright-field images of neurons under study, the morphology of the neurons could nevertheless be imaged using the fluorescence of a cytosolic fluorescent protein that had been expressed in these neurons. Cultured rat hippocampal neurons at DIV 17 expressing DsRed1-N1 were fixed in PBS containing paraformaldehyde (3.75%), glutaraldehyde (0.25%) and sucrose (4%) at 37° C. for 25 min and examined using both a 20× dry lens and a 63× oil-immersion lens under confocal microscopy. DsRed1-N1 was found in all parts of the neuron (FIGS. 3A and 3B). Some small structural features, such as the dendritic spines (indicated by arrows in FIG. 3C), could be clearly discerned in the fluorescence image, but this was difficult to do in the bright-field image of the same neuron (FIG. 3D).

The medium in the live-cell observation chamber could be heated and cooled rapidly and reversibly When the live-cell chamber was placed under a confocal microscope and observed using a dry lens, the temperature of the medium in the chamber could be changed rapidly and reversibly between 37° C. and 4° C. with heating and cooling rates of 0.35±0.04° C./s and 0.14±0.02° C./s (mean±S.D., n=5), respectively (FIG. 4A). When the same experiment was performed while the chamber was observed using a oil-immersion lens, the temperature of the medium in the chamber could also be changed reversibly between 37° C. and 8° C. with heating and cooling rates of 0.25±0.02° C./s and 0.09±0.01° C./s (mean±S.D., n=5), respectively (FIG. 4B). In the above experiments, the flow of ice-cold water in the circulation plate was stopped during the heating phase and turned on during the cooling phase.

The medium in the live-cell observation chamber could be changed rapidly and reversibly When medium containing a fluorescent dye, FITC (1.25 mg/ml, 706 μl), was introduced into the chamber via the sample injection valve, the change in the intensity of fluorescence in a central and a peripheral circular region (0.79 mm in diameter) was monitored under a confocal microscope and quantified (circles A and B in FIG. 5). It was found that the fluorescent dye started to appear in the central and peripheral regions of the chamber 5 sec after the injection valve was closed. The fluorescence intensities in both regions reached a plateau 5 sec latter and remained at the plateau for another 9 sec. At ~150 sec later, the fluorescence intensities had returned to the basal level. It was further found that the plateau fluorescence intensities of circular regions A and B were about 96% of those when the chamber was filled with the original FITC (1.25 mg/ml) solution. This observation indicated that this live-cell observation chamber could be used to monitor changes in neurons when they were subjected to rapid pharmacological manipulation.

Figure 6:
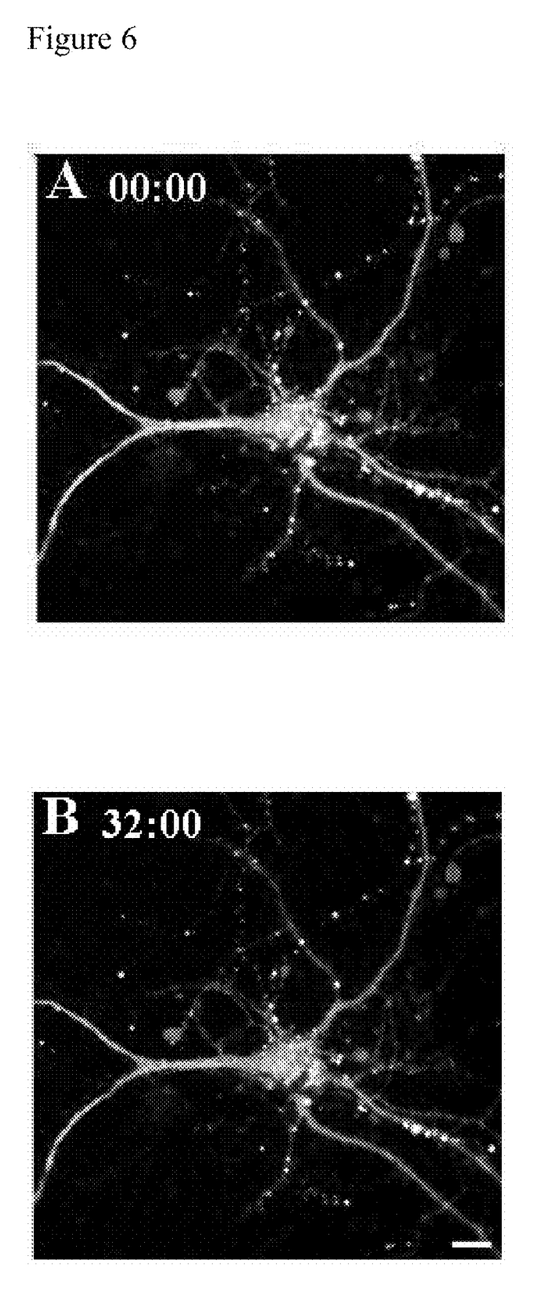

Neurons in the live-cell observation chamber could be examined for prolonged periods of time Cultured rat hippocampal neurons expressing YFP-α-tubulin at DIV 21 were maintained in the live-cell observation chamber at 37° C. and examined under a confocal microscope using an oil-immersion lens. The image of the same field was taken every 2 min without making any adjustments of the lens. At 30 min, it only required an adjustment in the Z-axis by 0.175 μm (and by 0.27 μm in a second experiment) to bring the image into focus again. In addition, no apparent difference in the fluorescence images of neurons taken before and after this experiment was noticeable (FIG. 6). This observation and those that would be described later indicated that the live-cell observation chamber described here was suitable for conducting experiments over periods of at least 30 min.

Cooling affects the dynamics of the microtubule cytoskeleton of neurons

Figure 7:
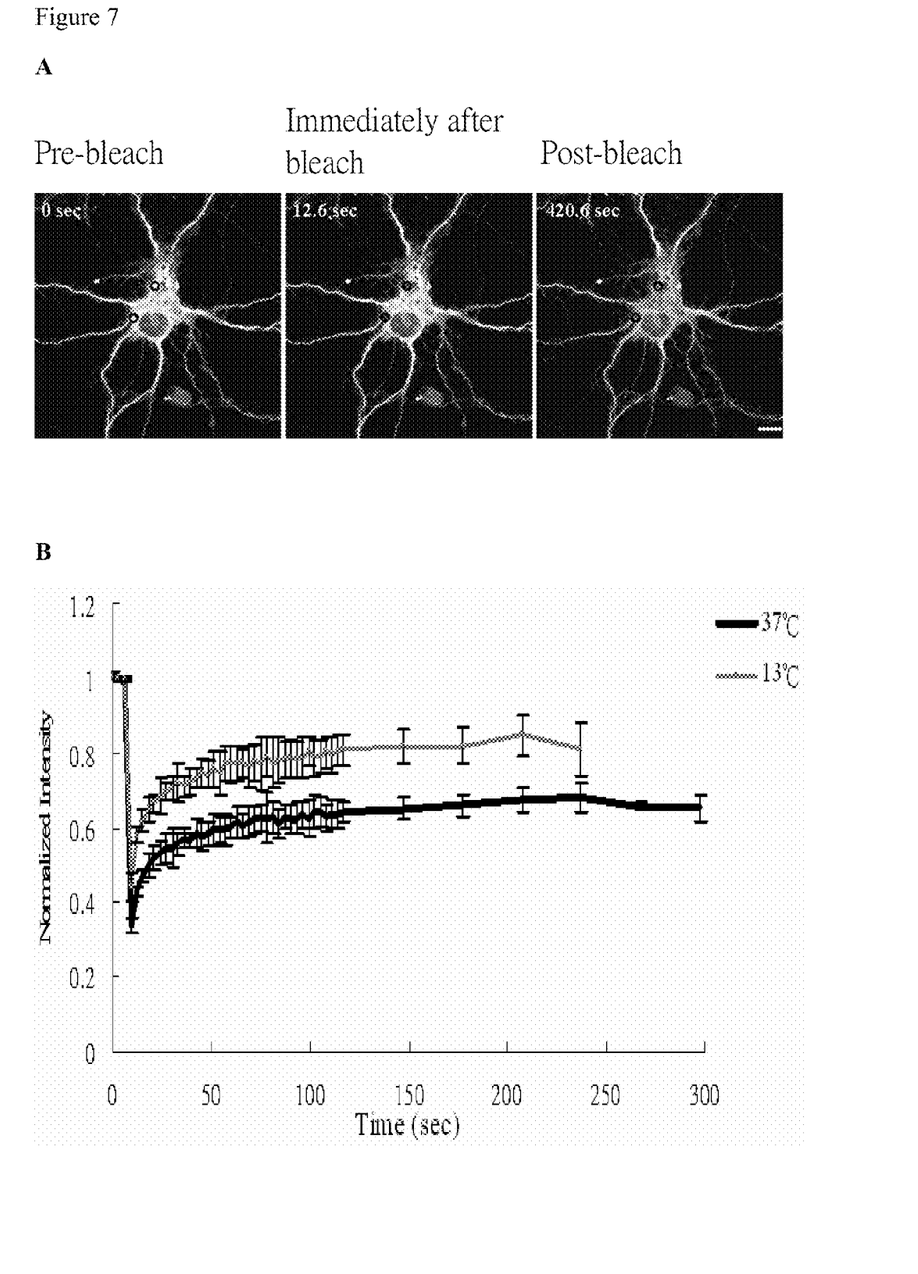

Cultured rat hippocampal neurons at DIV 17-21 expressing YFP-α-tubulin were maintained at 37° C. or 13° C. in the live-cell observation chamber and examined by confocal microscopy. FRAP of the YFP fluorescence in two regions of interest (ROI) was performed. Images of the neurons maintained at 37° C. during the course of the FRAP experiment were taken (three images taken at 0, 12.6 and 420.6 sec are shown in FIG. 7A) and the change in the fluorescence intensity of the ROI during the course of the experiment was quantified (lower curve in FIG. 7B). The same experiment, except for a shorter data acquisition duration of 150 sec, was performed with neurons maintained at 13° C. (upper curve in FIG. 7B). The pre-bleach intensity was normalized to 100%. Immediately after bleach at 37° C. and 13° C., the YFP-α-tubulin fluorescence intensity in the photobleached region dropped to 33.5±1.9% and 44.7±0.8% (mean±S.D., n=3), respectively. During the first 15 after photobleaching, the fluorescence recovered to 53.2±3.2% and 66.3±1.8% (mean±S.D., n=3), respectively. Finally in the ~8.5 min and ~2.5 min observation periods, the fluorescence slowly recovered to 68.3±3.8% and 79.3±3.1% (mean±S.D., n=3) of the initial intensity, respectively. The recovery of fluorescence in the ROI was fitted to a two-exponent equation as following:

$$I = 1 - [I_1] \times [\exp(-t/T_1)] - [I_2] \times [\exp(-t/T_2)],$$

where I is the normalized fluorescence intensity, $T_1$ and $T_2$ are the times for the first and second phase respectively, $I_1$ and $I_2$ are the mobile fractions of first and second phase respectively and t is the actual time. The resultant $T_1$, $T_2$, $\tau_{1/2,1}$ and $\tau_{1/2,2}$ values are summarized in Table 1.

TABLE 1

Coefficients for the two-phase exponential curves.

$I = 1 - [I_1] \times [\exp(-t/T_1)] - [I_2] \times [\exp(-t/T_2)]$

|  | $T_1$, sec | $\tau_{1/2,1}$, sec | $T_2$, sec | $\tau_{1/2,2}$, sec |
|---|---|---|---|---|
| 37° C. | 14.9 ± 5.3 | 10.3 ± 3.7 | 125.1 ± 28.0 | 86.7 ± 19.4 |
| 13° C. | 8.8 ± 1.6 | 6.1 ± 1.1 | 60.3 ± 8.8 | 41.8 ± 6.1 |

At 37° C., the $\tau_{1/2}$ values for the first and second phase were 10.3±3.7 s and 86.7±19.4 s, respectively; furthermore, the $T_1$ and $T_2$ values were 14.9±5.3 s and 125.1±28.0 s respectively. At 13° C. the $\tau_{1/2}$ values for the first and second phase were 6.1±1.1 s and 41.8±6.1 s, respectively, and the $T_1$ and $T_2$ were 8.8±1.6 s and 60.3±8.8 s, respectively. Since the microtubule cytoskeleton of the neurons maintained at 13° C. exhibited a bigger mobile fraction and faster recovering rates (or shorter $t_{1/2}$ values) than neurons maintained at 37° C., these results indicated that the microtubule cytoskeleton in neurons maintained at 13° C. was more mobile than that in neurons maintained at 37° C.

Cold-Sensitive Localization of α-Tubulin in the Dendritic Spines of Neurons

Dendritic spines are small protrusions on the dendrites of neurons and the target of the majority of excitatory inputs in mammalian CNS (Alvarez V. A. and Sabatini B. 2007. Anatomical and Physiological Plasticity of Dendritic Spines. Annu. Rev. Neurosci. 30: 79-97; Bourne J. N. and Harris K. M. 2008. Balancing Structure and Function at Hippocampal Dendritic Spines. Annu. Rev. Neurosci. 31: 47-67.). Cultured rat hippocampal neurons co-transfected with the plasmids of YFP-α-tubulin and DsRed1-N1 at DIV17 were maintained in a live-cell observation chamber with the temperature of medium kept at 37° C., except for one period of 6 min at 13° C. At 37° C., nearly all the dendritic spines, which were outlined by DsRed1-N1 fluorescence, contained YFP-α-tubulin (top row panels of FIG. 8A). When the temperature of medium was cooled to 13° C., the YFP-α-tubulin fluorescence was found to have receded from more than half of the spines (middle row panels of FIG. 8A), but the shape of dendritic spines maintained largely unchanged over the same period. Upon returning the temperature of the medium to 37° C. again, YFP-α-tubulin was found to reappear in nearly all of the spines (bottom row panels of FIG. 8A). Schematic representation of the various types of changes in YFP-α-tubulin (blue) in dendritic spines before, during and after the intermittent period of cold are summarized in FIG. 8B. Spines were categorized in terms of their changes in YFP-α-tubulin distribution and shape into three types (from top to bottom in FIG. 8B). These were those where the YFP-α-tubulin immunoreactivity reversibly receded from the spine structure during the cold shock experiment, those that developed as newly formed YFP-α-tubulin-positive spines during the experiment and those that exhibited no changes in spine shape or YFP-α-tubulin distribution during the experiment. These three types of spines accounted for 57.9±6.7%, 0.6±1.4% and 41.5±6.8% of the 144 spines found on seven neurons. The results indicated that the appearance of α-tubulin in the dendritic spines was cold-sensitive and this was consistent with an earlier in vitro study (Cheng H. H. et al. 2009. Cold-Induced Exodus of Postsynaptic Proteins From Dendritic Spines. Journal of Neuroscience Research 87: 460-469.).

The Caffeine-Induced Exit of α-Tubulin from Dendritic Spines

Cultured rat hippocampal neurons co-transfected with YFP-α-tubulin and DsRed1-N1 at DIV17 were maintained in a live-cell observation chamber at 37° C. Medium containing 10 mM caffeine was then introduced into the chamber. After 10 min, the medium containing caffeine was replaced by fresh medium. Before caffeine treatment, nearly all dendritic spines outlined by DsRed1-N1 fluorescence showed the presence of YFP-α-tubulin fluorescence (top row panels of FIG. 9A). In the presence of caffeine, YFP-α-tubulin fluorescence was found to recede from more than half of spines (middle row panels of FIG. 9A). YFP-α-tubulin fluorescence was found again in most dendritic spines 5 min after the caffeine-containing medium was replaced by fresh medium (bottom row panels of FIG. 9A). Based on the changes in the YFP-α-tubulin distribution and spine shape, the spines were also categorized into three types, namely those exhibited reversibly receding YFP-α-tubulin, those that developed as newly formed YFP-α-tubulin-positive spines and those that exhibited no changes in YFP-α-tubulin distribution or spine shape during caffeine treatment. The three types of spines respectively accounted for 49.6±4.2%, 0.5±1.4% and 49.9±2.9% of the 122 spines on six neurons. Caffeine is an activator of ryanodine receptors, which were present on the endoplasmic reticulum that was found in the dendritic spines. It was likely that caffeine application activates the ryanodine receptors, which led to a rise in cytoplasmic calcium. This elevation of intracellular calcium would then seem to result in the exit of α-tubulin from dendritic spines by a mechanism as yet unclear.

While the invention has been described and exemplified in sufficient detail for those skilled in this art to make and use it, various alternatives, modifications, and improvements should be apparent without departing from the spirits and scope of the invention.

One skilled in the art readily appreciates that the present invention is well adapted to carry out the objects and obtain the ends and advantages mentioned, as well as those inherent therein. The cells, viruses, and processes and methods for producing them are representative of preferred embodiments, are exemplary and not intended as limited on the scope of the invention. Modifications therein and other uses will occur to those skilled in the art. These modifications are encompassed within the spirit of the invention and are defined by the scope of the claims.

What is claimed is:

1. A cell observation equipment for a non light-transmitting microscope, comprising:
   (a) a coverslip;
   (b) a sealed material;
   (c) a microchamber plate containing a circular groove embedded with the sealed material; an inner circular opening to load and circulate a medium; and a plurality of pipes connecting with the inner circular opening; and
   (d) a thermal effect heat pump placed below the microchamber plate by way of contacting directly,
   wherein the coverslip is placed on the inner circular opening of the microchamber plate,
   wherein the sealed material is placed between the coverslip and the microchamber plate to keep the chamber leak free,
   wherein the pipes include the pipe for inflow of the medium, the pipe for outflow of the medium, and the pipe for temperature detection.

2. The cell observation equipment of claim 1, wherein the non light-transmitting microscope is a confocal microscope or a fluorescence microscope.

3. The cell observation equipment of claim 1, wherein the thermal effect heat pump is a thermoelectric Peltier effect heat pump.

4. The cell observation equipment of claim 3, wherein the thermoelectric Peltier effect heat pump acts as a heater or a cooler by switching the polarity of input DC current.

5. The cell observation equipment of claim 1, wherein the microchamber plate is made of a transparent and non heat conducting material.

6. The cell observation equipment of claim 5, wherein the transparent and non heat conducting material is polymethyl methacrylate.

7. The cell observation equipment of claim 1, the sealed material is silica gel or rubber-like cushion.

8. The cell observation equipment of claim 1, which comprises a sample injection valve connected with the inflow pipe.

9. The cell observation equipment of claim 1, wherein the inflow and outflow of the medium is driven by mechanical power.

10. The cell observation equipment of claim 1, which further comprises a circulating plate attached below the thermal effect heat pump directly.

11. The cell observation equipment of claim 10, wherein the circulating plate contains a channel for flow of a cooling liquid.

12. The cell observation equipment of claim 11, wherein the flow of the cooling liquid is driven by the gravity or mechanical power.

13. The cell observation equipment of claim 12, wherein the flow of the cooling liquid is used to enhance the cooling effect of the thermal effect heat pump.

14. The cell observation equipment of clam 1, which is applied to change the temperature of the medium rapidly and reversibly.

15. A method for observing the influence to a cell by changing the temperature rapidly, the steps comprising:
   (a) culturing the cell attached on one side of a coverslip;
   (b) constructing the cell observation equipment of claim 1, wherein the cell is faced to the microchamber plate;
   (c) inputing a current to the pump and adjusting a direction of the current to heat or cool the microchamber plate; and
   (d) observing a cell performance after heating or cooling rapidly.

16. The method of claim 15, which further comprises the step of attaching the circulating plate below the thermoelectric Peltier effect heat pump to enhance the cooling effect of the thermoelectric Peltier effect heat pump.

* * * * *